United States Patent [19]
Adolf et al.

[11] Patent Number: 5,334,180
[45] Date of Patent: Aug. 2, 1994

[54] STERILE FORMED, FILLED AND SEALED FLEXIBLE CONTAINER

[75] Inventors: Wayne F. Adolf, Mt. Prospect; R. Hayes Helgren, Mundelein; James T. Renick, Bristol; Walter T. Szempruch, Gurnee, all of Ill.

[73] Assignee: Abbott Laboratories, Abbott Park, Ill.

[21] Appl. No.: 41,797

[22] Filed: Apr. 1, 1993

[51] Int. Cl.5 .................................. A61B 19/00
[52] U.S. Cl. ...................... 604/411; 604/905; 383/67; 383/906; 222/81
[58] Field of Search ............ 604/86, 87, 88, 408, 604/411, 905; 383/67, 906; 222/81, 82, 83, 83.5, 84–91

[56] References Cited

U.S. PATENT DOCUMENTS

| | | | |
|---|---|---|---|
| Re. 29,656 | 6/1978 | Chittenden et al. | 222/83 X |
| 2,726,656 | 12/1955 | Lockhart | 222/81 |
| 3,509,879 | 5/1970 | Bathish et al. | 604/408 |
| 3,986,507 | 10/1976 | Watt | 604/408 |
| 4,195,632 | 4/1980 | Parker et al. | 604/411 |
| 4,381,776 | 5/1983 | Lathan, Jr. | 604/411 X |
| 4,432,755 | 2/1984 | Pearson | 604/411 X |
| 4,650,452 | 3/1987 | Jensen | 604/408 X |
| 4,686,125 | 8/1987 | Johnston et al. | 604/408 X |
| 4,781,679 | 11/1988 | Larkin | 604/88 |
| 5,098,202 | 3/1992 | Rosenbaum | 604/408 X |
| 5,176,673 | 1/1993 | Marucchi | 604/411 X |

Primary Examiner—Randall L. Green
Assistant Examiner—Mary Beth O. Jones
Attorney, Agent, or Firm—A. Nicholas Trausch

[57] ABSTRACT

The present invention relates to a sterile form, filled and sealed flexible solution container and an attached port assembly that allows for the sterile dispensing of the solution.

14 Claims, 7 Drawing Sheets

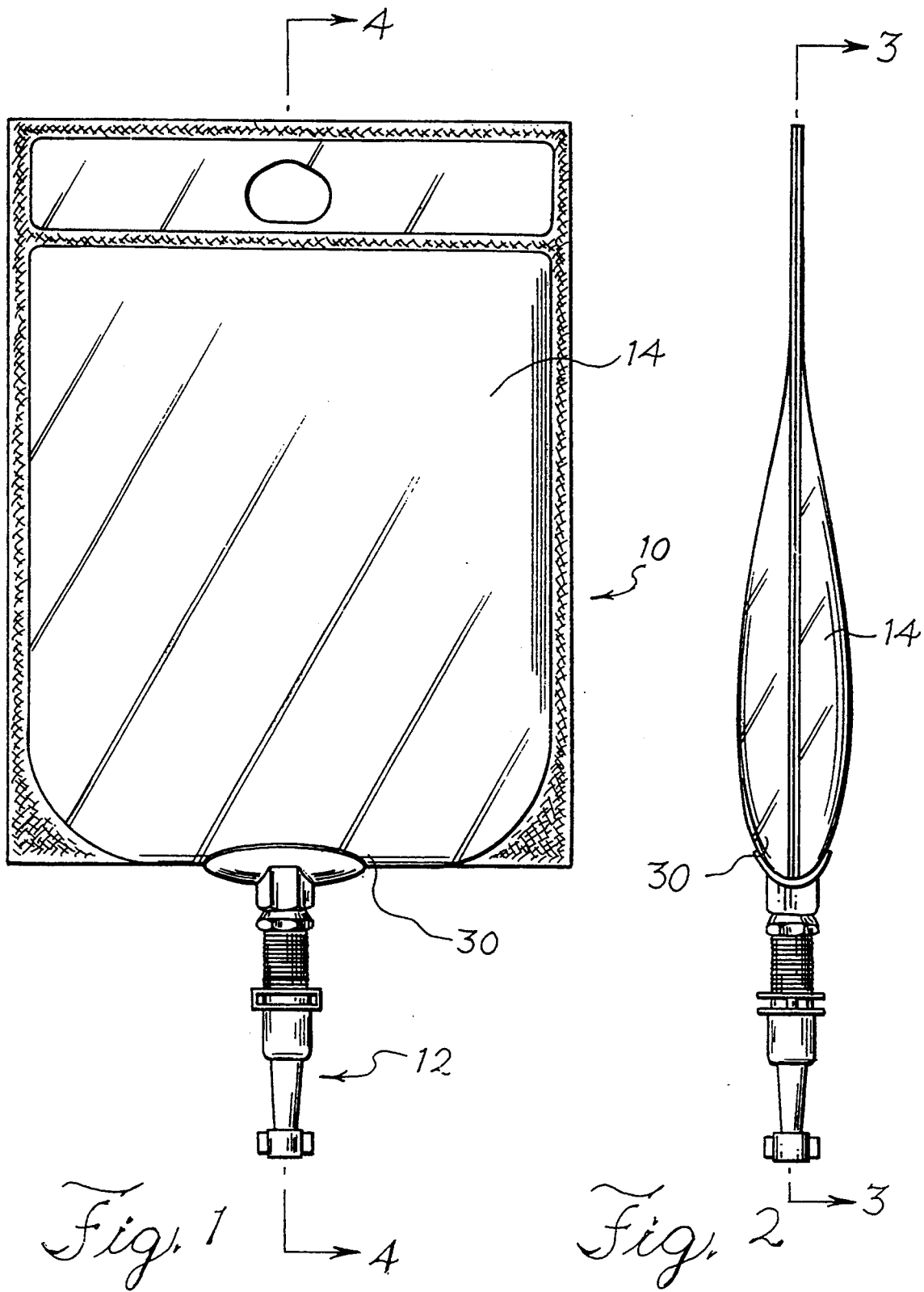

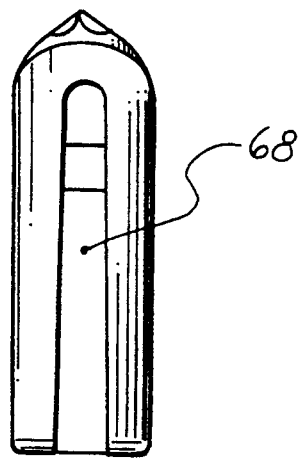
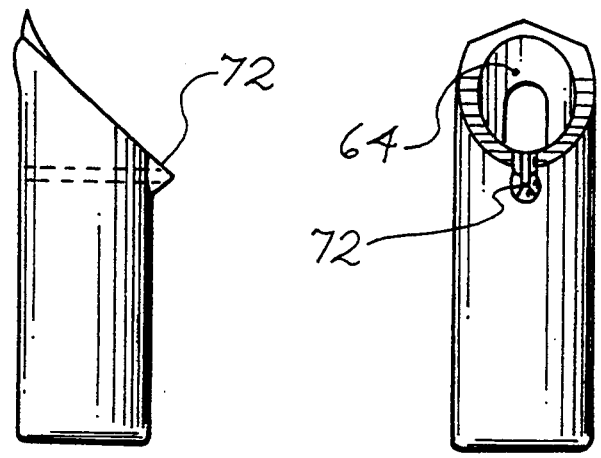
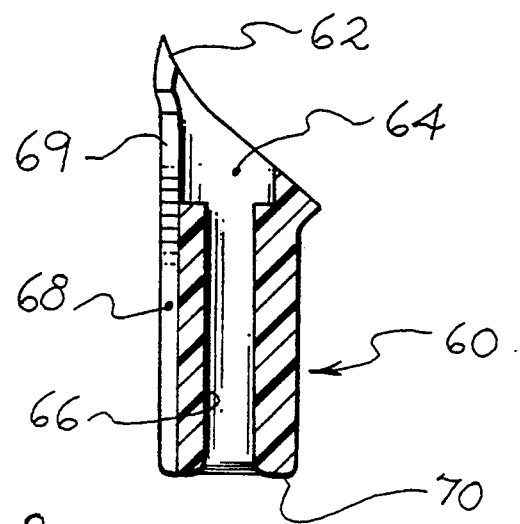
Fig. 8E
Fig. 8D  Fig. 8B  Fig. 8C
Fig. 8A

STERILE FORMED, FILLED AND SEALED FLEXIBLE CONTAINER

FIELD OF THE INVENTION

The present invention relates to a sterile formed, filled and sealed flexible solution container with an attached administration port system and, in particular, to a sterile formed, filled and sealed flexible solution container and an attached sterile administration port assembly which allows for the sterile maintenance and delivery of a sterile medical solution.

BACKGROUND OF THE INVENTION

Various foodstuffs, liquids and other degradable material can be sterilely packaged in pouch-type flexible containers made from webs of flexible film that are sealed together along the unconnected peripheral sides. This type of flexible packaging is commonly referred to as form, fill and seal packages. There are a number of advantages to these pouch-type flexible containers, including weight, durability and low cost to produce. To a lesser extent, a few medical solutions have been sterilely packaged in pouch-type flexible containers by form, fill and seal packaging machines.

One disadvantage of these pouch-type flexible containers for medical solution use is that it is difficult to make a sterile connection to the flexible container for drawing the contents in a sterile manner. The wall material of the container is flexible and without any rigidity. Thus, it is difficult to obtain a liquid tight and leakproof connection through the flexible wall using traditional medical connectors such as needles or piercing pins.

Traditionally, it has been necessary for flexible solution containers used for parenteral solutions to include rigid administration ports to facilitate sterile access to the solution. These pre-formed, rigid administration ports are often molded from a suitable medical grade plastic material. The usual considerations for the material used for the administration ports are the ease of molding and the ability to be securely bonded to the flexible film sheets. For example, a "boat" administration port may be sealed by many known thermal bonding processes between the opposed inner layers of two flexible film sheets so as to form a flexible solution container. Ultrasonic welding or solvent bonding may also be used to seal the boat port between the film layers.

The majority of flexible films used for flexible solution containers are monolayer PVC films. Recently, a few multiple-layer, extrusion or adhesive laminated films have been used in form, fill and seal packaging for producing flexible solution containers. The inner, solution contacting layer must be substantially inert to the solution. Also the inner layer of the film must be readily bondable to itself. Furthermore, the inner film layer must be compatible with any material used for attachable components, such as administration ports. The outer layer of the laminated film must be durable and also compatible with other materials that may contact or be attached to the outside surface. If neither the inner or outer layer has the desired solution maintaining and barrier characteristics, such as low moisture and/or oxygen permeability, additional film layers may be required between the inner and outer layers.

A primary disadvantage of known flexible solution containers assembled according to the above described boat port construction is that the port material typically has a higher oxygen permeability than the film material. In the known form, fill and seal flexible solution containers, the permeability characteristic of the port material is much greater than the similar characteristic for the laminated film used to make the flexible container. Thus, the administration port of known flexible solution containers is often the weakest part of the barrier characteristics. This factor becomes extremely important for certain medical solutions which are sensitive to oxygen or other penetrating gases, for example.

In the past, any of the above deficiencies has been overcome by overwrapping the flexible solution container and/or the administration ports, with an overwrap material. While this redundancy in packaging may provide the desired barrier characteristics, the overwrap material introduces two important disadvantages. First, there is the additional cost to fabricate and later dispose of the overwrap. Second, there is concern that extractables from the overwrap material may migrate into the contained solution during post filling procedures, such as during the sterilization process or even during shelf life.

Pre-formed rigid administration ports constitute potential places of leakage and are potential points of entry in an otherwise sealed, durable flexible container. Moreover, the rigid ports make it more difficult to arrange an outer protective package around the flexible container. Also the protective overwrap only initially prevents the packaged solution from losing its potency due to evaporation or diffusion. When the overwrap is removed or breached, the administration ports positioned between two layers of film is an effective breach in the barrier characteristics of the flexible container for certain sensitive drugs.

For example, due to the sensitivity of certain solutions to oxygen, such as amino acids, it is desirable to use materials that minimize the permeation of oxygen for the flexible solution containers for parenteral administration of these solutions. The properties of the film can be controlled easily by the choice of the film components and structure. However, the oxygen permeation properties of the port system are not as easily controlled. Thus, it is desirable to use the film and its good barrier properties as both the solution contacting surface and the pierceable diaphragm of the administration port system so that the barrier properties of the port system are consistent with the barrier properties of the flexible container. However this consistency is not achieved in known flexible containers having pre-formed rigid port systems sealed between the film layers of the flexible container.

Moreover, the known flexible container and administration port systems often include an entry port in addition to the administration port. The entry ports are likewise inserted between film layers at the perimeter seal. Both ports are thus a breach through an otherwise effective perimeter barrier. A pierceable diaphragm is provided in the administration port to prevent an outflow of solution. During packaging, the flexible container may be filled through the entry port. After filling, the entry port is sealed, but the ports, and specifically the exposed port material, is the potential point of entry for compromising the barrier characteristics.

Flange ports are an alternative to boat ports and may be advantageously sealed to a film surface. However for the flexible solution container produced by the known form, fill and seal process, the use of flange ports does not remove the barrier deficiency. For example, a flexible parenteral solution container including a flange-sealed port assembly is disclosed in U.S. Pat. No. 4,695,337 to Christine and in U.S. Pat. No. 4,779,397 to Christine et al. A major disadvantage of the disclosed flexible solution container is that the flexible film barrier of the flexible container is purposefully breached during the assembly steps to mount and seal the administration port or fitment to the inside surface of the flexible container, as seen for example in FIGS. 4a–4d of the patents.

Thus, due to the inherent breaches in the film barriers for known flexible solution containers in current use, parenteral solutions may be subjected to degradation during the shelf life of the product solution. While an overwrap may provide some protection for the flexible container and the port administration system from contamination or degradation during shelf life, the overwrap introduces additional concerns that are increasingly desirable to avoid.

Thus, it is desirable to utilize the unbreached and completely intact film of the flexible solution container as the primary barrier for medical solutions packaged in flexible solution containers and especially for certain oxygen or other gas sensitive parenteral solutions.

It is therefore desirable to manufacture a flexible container that provides integral barrier characteristics without any compromises in the barrier characteristics of the film material used for the flexible solution container.

It is also desirable to manufacture a flexible container that includes an attached administration port system that is accessible by a variety of piercing pins, including center point pins, beveled pins and blunt pins as well as a port system that is compatible with the various lengths and other dimensions of the most common piercing pins.

It is also desirable to manufacture a flexible container that allows the maximum amount of solution to be readily, completely and easily delivered in a sterile manner from the container.

SUMMARY OF THE INVENTION

The present invention relates to a sterilely formed, sterilely filled, and sterilely sealed flexible solution container including a sheet of laminated flexible film folded over along a saddle line so that a portion of the inner surface of the sheet faces a second portion of the inner surface of the sheet. A continuous peripheral line of sealing contact along the perimeter of the facing portions of this sheet is provided so as to form an inner sealed chamber between the first and second facing portions of the film A rigid administration port including a tubular member having a first and second open end is provided for attachment to the outer surface of the flexible container. An integral circumferential flange surrounds the first open end of the tubular port and the flange is circumferentially sealed generally along the axis of a sump portion outwardly formed in the bottom surface of the flexible film of the formed, filled and sealed chamber. The integrity of the sealed chamber is not compromised by the attached tubular port. An access fitment is provided on the second open end of the tubular port and a removable cover for closing the second open end is provided. A penetrator element is slidably contained within the tubular port and has a contained sharp end for slidably protruding beyond the circumferential flange at the first open end of the tubular port member so as to pierce the film surface and penetrate the sealed chamber. At least one fluid passageway through the penetrator element from the pierced sealed chamber to the access fitment is provided.

More specifically, the present invention relates to an administration port for use with a formed, filled and sealed, flexible solution container. The port includes a rigid, tubular body having a first and second open end. A circumferential flange surrounds the first open end of the tubular body and is circumferentially sealable to the outer surface of the flexible container. An access fitment is provided at the second open end of the tubular body. A resilient or elastomeric cover is removably attached to the access fitment to initially close the second open end of the tubular body and maintain the sterile condition of the port system until used. A piercing mechanism or penetrator is provided in the administration port to initiate fluid flow communication from the sealed flexible container to the access fitment. In a preferred embodiment, the penetrator element includes a slidably cylindrical member initially wholly contained within the tubular body. The penetrator has a sharp end for slidably protruding beyond the circumferential flange so as to pierce the film forming the sealed inner chamber. The penetrator includes a hollow portion opening into the sharp beveled edge at the front end. A passageway is provided through the penetrator element from the pierced surface of the sealed container to the access fitment for sterile fluid flow of the solution from the flexible container.

The present invention is also directed to a sterile method for forming, filling and sealing a continuous, longitudinal strip of flexible laminated film into a plurality of individual flexible containers. The continuous film strip enters the sterile core and is sterilized and dried by any suitable sterilizing process. The flat, continuous film strip is continuously indexed through the sterile core. Next a plurality of center portions are outwardly stretched to form a plurality of discrete fluid sumps. The continuous film strip is then formed into a continuous U-shaped trough having a rounded bottom surface and two inside facing surfaces. Transverse portions of the sides surfaces are sealed together and with the bottom surface forms an open pocket. The pocket is filled with a seperately sterilized solution and the top surface is sealed to form sealed chambers. As a final step, the continuous strip is cut coincident with each transverse seal so as to form individual flexible solution containers.

Other feature and advantages of the present invention will become readily apparent from the following detailed description, the accompanying drawings, and the appended claims.

BRIEF DESCRIPTION OF THE DRAWINGS

FIG. 1 is a elevation view of a filled and ready to use flexible solution container and the attached port assembly according to the present invention;

FIG. 2 is a side view of the filled flexible solution container and the attached port assembly of FIG. 1;

FIG. 8A is a cross section view of the penetrator element according to the present invention;

FIG. 8B is a elevation view of the penetrator element of FIG. 8A;

FIG. 8C is a right side view of FIG. 8B;

FIG. 8D is a left side view of FIG. 8B;

FIG. 8E is a top end view of FIG. 8B;

DESCRIPTION OF THE PREFERRED EMBODIMENT

Referring now to FIGS. 1–2 and 3–4, a flexible solution container 10 and port assembly 12 for maintenance and delivery of a sterile medical solution is shown. The flexible container is fabricated from a sheet of flexible, multiple-layer film, such as for example an extrusion laminated film or an adhesive laminated film. The laminated film has at least an inner bondable layer, the desired barrier layers, and an outer bondable layer. The port assembly components are molded of suitable materials that are attachable by a saddle flange to the outer film layer, preferably by a thermal bonding process.

Figure 12:
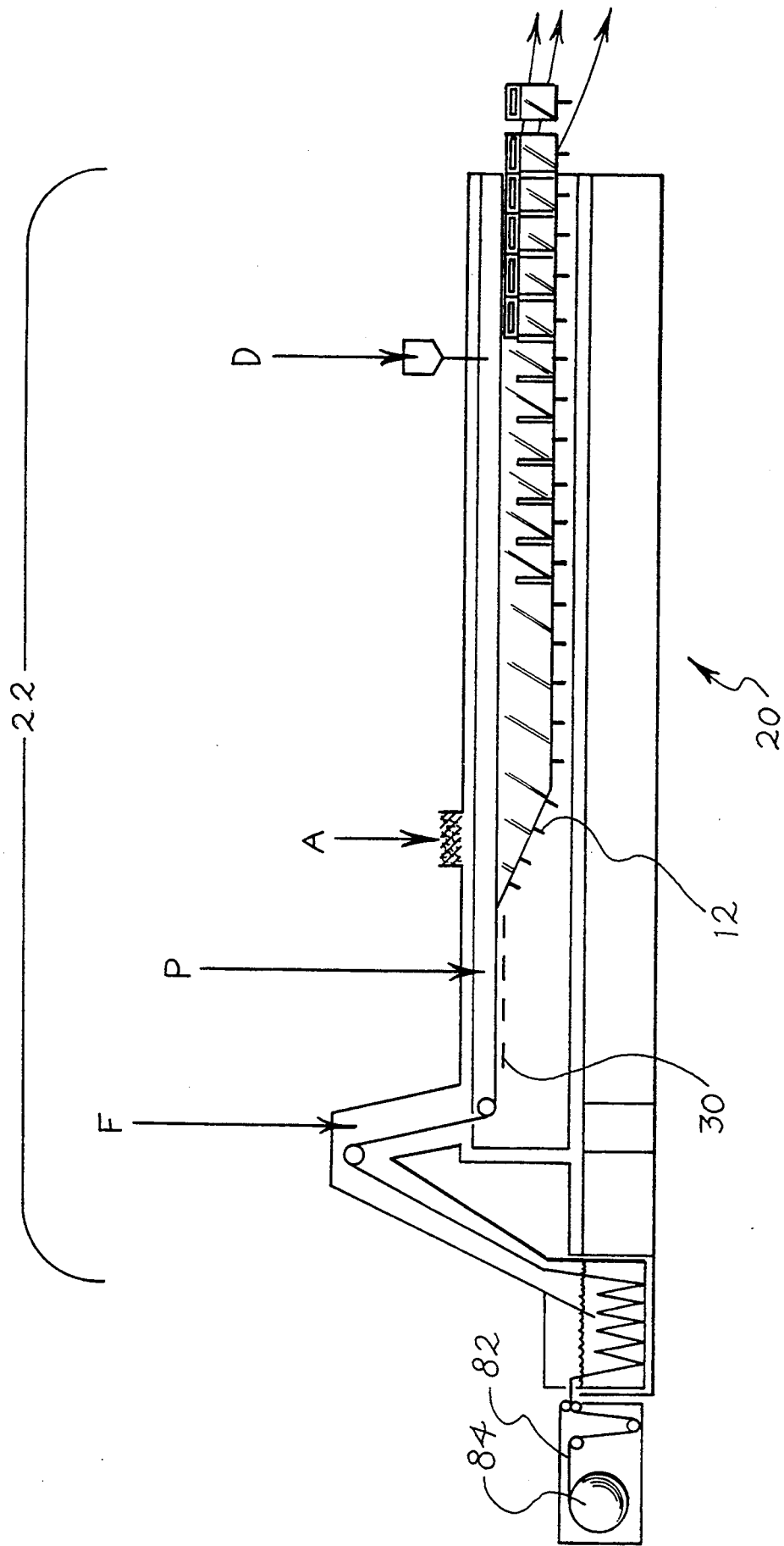
FIG. 12 is a schematic depiction of a form, fill and seal packaging machine and sterile core that might be use to assemble the flexible solution container and port assembly according to the present invention.

The flexible container is preferably manufactured by a form, fill and seal packaging machine 20 as schematically depicted in FIG. 12. The forming of the flexible container, the filling with a sterile solution and the sealing of the flexible container is performed in a sterile core environment 22 associated with the packaging machine. The product solution is sterilized outside of the sterile core. The product solution is maintained sterile as it is filled and sealed in the flexible container. The port assembly is pre-sterilized outside of the sterile core and attached to the flexible container in the sterile core. The packaged product is thus a sterile solution in a sterile container with an attached sterile port assembly that is suitable for medical use such as parenteral fluid administration.

An example of a multiple-layer film that is suitable for form, fill and seal processing into a flexible container is as follows. A multiple layer, extrusion laminated film has a bondable inside layer, a gas barrier layer, a thermal stability layer, appropriate bonding layers and bondable outside layer.

The laminated film sheet is initially horizontally flat as it longitudinally enters the packaging machine. A longitudinal middle line, hereafter refered to as the saddle line longitudinally divides the film sheet into substantially equal and mirror-image first and second portions.

A plurality of discrete, outward (i.e. downward) extending fluid sumps 30 are formed generally along the saddle line, such that the longitude axis of the sump is coincident with the saddle line. The sump is created by a thermo-forming process. The relevant portion of the film is heated and permanently stretched outward. The sump preferably has a smooth interior radius. The sump can be formed by permanently stretching the film beyond recovery by applying heat and a forming mandrel from the inside layer, or by applying heat and drawing a vaccuum from the outside surface, or a combination of these or other known thermo-forming processes.

First and second portions of the film sheet are then inwardly folded over the saddle line so as to form a U-shaped through. The bottom surface 40 of the trough includes the stretched fluid sump 30. The saddle flange of the port member is attached to the outside surface of the laminated film at the sump 30.

Figures 3, 4:
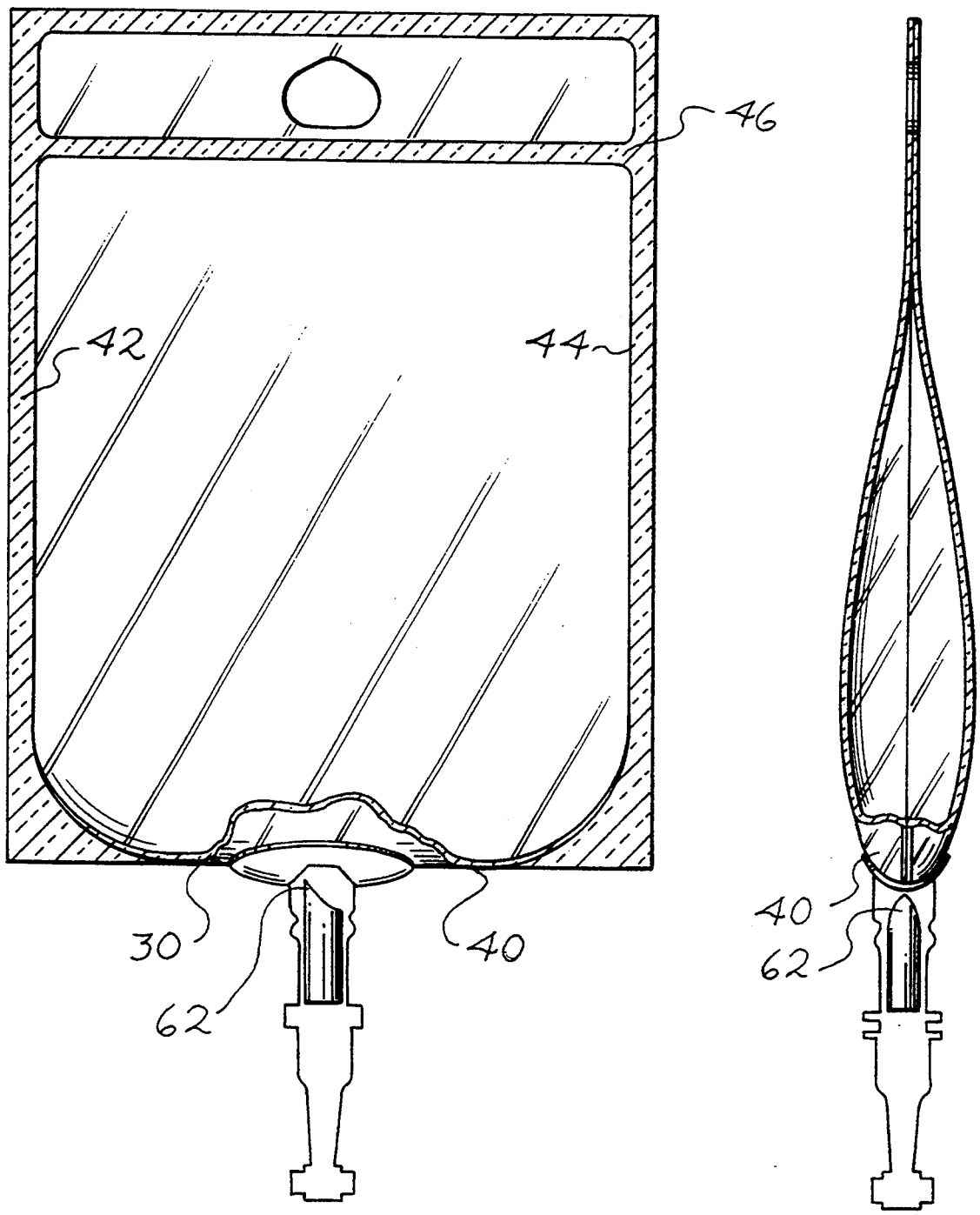
FIG. 3 is a elevation cross section view of the preferred embodiment of the flexible solution container and attached port assembly according to the present invention.
FIG. 4 is a side cross section view of FIG. 3.
Figure 5:
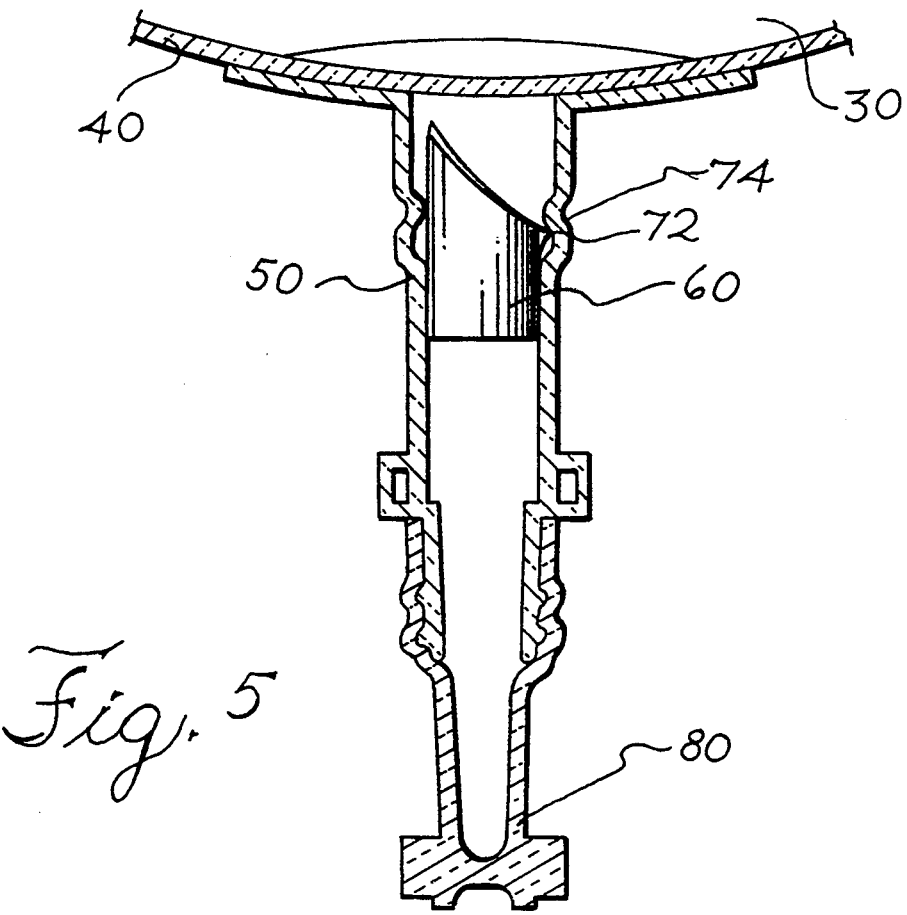
FIG. 5 is a partial cross section of the assembled port system according to the present invention.
Figure 6:
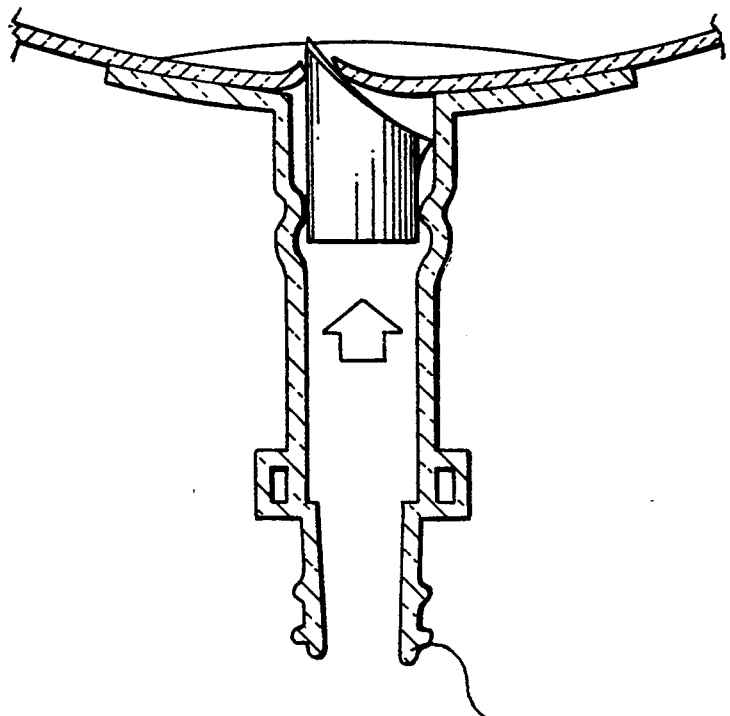
FIG. 6 is a partial cross section similar to FIG. 5 showing the penetrator element of the port system in the activated condition and in position for fluid flow.
Figure 7D:
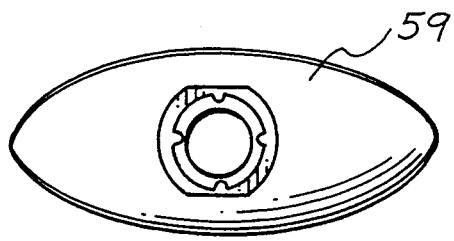
FIG. 7D is an end view along line D—D of FIG. 7B.
Figure 7E:
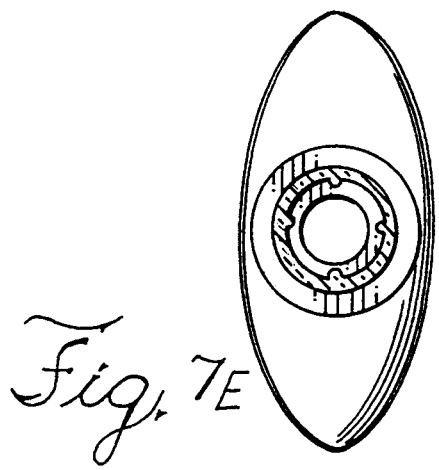
FIG. 7E is a sectional view along line E—E of FIG. 7C.
Figure 7B:
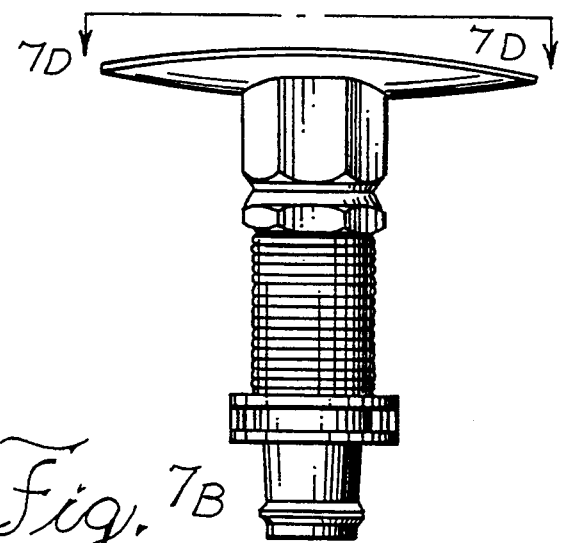
FIG. 7B is a elevation view of the port member of FIG. 7A.
Figure 7C:
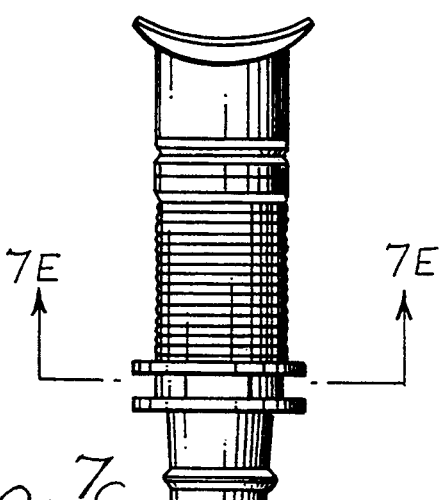
FIG. 7C is a side view of FIG. 7B.
Figure 7A:
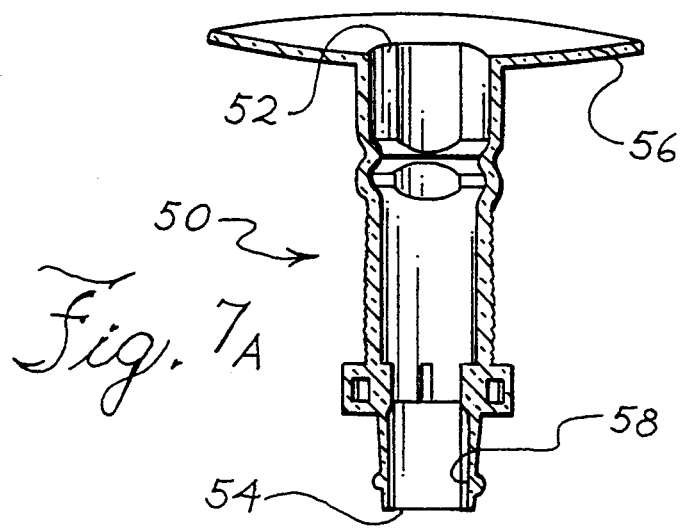
FIG. 7A is a cross section view of the tubular port member according to the present invention.

Refering now to FIG. 3 the inner layer of the opposed first and second laminated film portions are sealed together along a first sealing line extending from and generally perpendicular to the bottom surface 40 so as to form a first transverse side seal 42. The inner layer is also sealed together along a second sealing line parallel to the first line, but an equal distant on the other side of the fluid sump so as to form a second transverse side seal 44. Together the first side seal 42, the bottom surface 40 and the second side seal 44 form an open pouch.

The pouch may optionally be flushed with a flushing agent if it is to be filled with an oxygen sensitive drug. After the pouch is flushed and filled with the sterile solution, the top portion of the pouch is sealed together along a third sealing line 46 so as to form a hermetically sealed inner chamber between the first and second laminated film portions.

Refering now to FIGS. 5–8, the port assembly includes a rigid tubular member 50, a cylindrical penetrator element 60, and a cover member 80. The tubular port member 50 has a first 52 and second 54 open end and is molded preferably of a heat bondable medical grade plastic, preferably a similar if not the same material as the inner layer of the laminated film. The tubular port member 50 is preferably injection molded from an olefin. The tubular port member includes an integral and circumferential flange 56 that surrounds the first open end of the tubular port. The flange has a contoured face of the same longitudinal and latitudinal shape as the outward stretched fluid sump. The congruent face of the contoured flange is circumferentially sealed around the orifice of the first open end of the tubular port so that there is an annular fluid tight seal between the inner face of the flange and the outer surface of the film layer at the fluid sump.

The second opened end 54 of the tubular port is provided with an access fitment 58 that doesn't leak when connected with most convention medical piercing pin connectors. A removable cover 80, preferably made of an injection molded material or a compression set resilient elastomer material, is provided for closing and maintaining the sterility of the second open end 54 of the tubular port.

Since the pierceable diaphragm of the port assembly according to the present invention is the laminated film material of the flexible container itself, a mechanism to pierce the film sheet and penetrate the inner chamber must be provided. In previously described flexible containers, the diaphragm element is located near the second open end of the port system. However, in the port system of the present invention, the diaphragm element is located at the first open end of the port system. Since there is little in common among known piercing pins, a captive piercing mechanism or penetrator 60, which functions as a universal piercing pin adapter for most of the known pins, is specifically provided for the port system of the present invention.

The cylindrical penetrator element 60 is slidably contained within the tubular port 50. The penetrator element is preferably molded of a polycarbonate material for example, and has a sharp, beveled end 62 for protruding beyond the circumferential flange so as to pierce the film sheet and penetrate the inner chamber. The sharp end of the penetrator element has a hollow chamber 64 forwardly opening onto the beveled face. At least one and preferably two fluid passageways are formed through the penetrator element from the sharp end for fluid communication with the penetrator hollow chamber 64. The primary passageway is a center throughbore 66 from the hollow chamber to the opposite end of the penetrator. The secondary passageway is a substantially longitudinally extended channel 68 along the cylindrical surface of the penetrator and connected radially to the hollow chamber 64. Thus the primary and secondary passageways provide fluid communication from the hollow chamber to the access port.

More specifically the tubular port member as shown in FIGS. 7A-7E includes a first 52 and second 54 open end. The port includes an integral circumferential flange 56 surrounding the first opening. The flange face is congruent with the stretched surface of the fluid sump 30 of the flexible container. The port assembly also includes a slidable cylindrical penetrator 60. The cylindrical penetrator has a hollow chamber 64 in the beveled end 62 at the first open end of the tubular member. Preferably the other, non-piercing end 70 of the sliding penetrator member is flat, as shown in the preferred embodiment. Alternatively, the penetrator could be symmetrical and have two beveled opposite ends for ease of assembly.

The penetrator includes a primary fluid passage such as a center bore 66 from the hollow chamber in the beveled end 62 of the penetrator through the cylindrical body of the penetrator. As best seen in FIGS. 8A and 8D, the penetrator 60 further includes a secondary longitudinal channel 68 substantially along the outer cylindrical surface of the penetrator. The channel is radially connected to the hollow chamber 64 at the beveled end of the penetrator by a radial connection passage.

The penetrator also includes a protruding knob 72 that is initially keyed within a radial shoulder 74 on the inner surface of the tubular port member 50 for initially holding the penetrator in the inactive position. The knob is also preferable keyed to a longitudinal channel in the port member so as to prevent the penetrator from twisting as it is activated and inserted through the laminated film and into the inner chamber. A rotational change in orientation of the penetrator could orient the sharp end 62 of the penetrator near the side wall of the flexible container and thus increase the risk of an accidental pin puncture of the side wall of the flexible container. The prefered orientation of the beveled end 62 is shown in FIG. 3 and 4 for example.

Figure 10A:
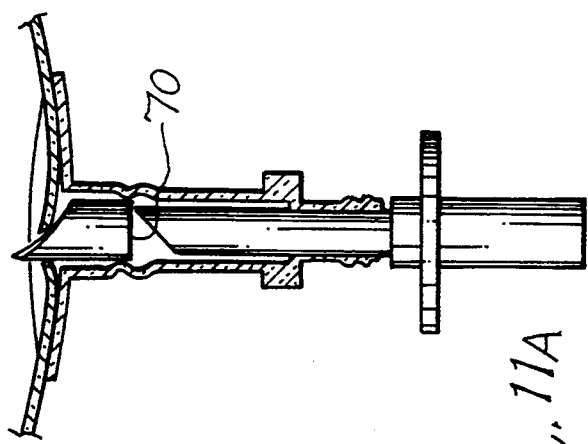
FIG. 10A is a partial cross section of the port assembly according to the present invention when activated by a blunt spiking pin.
Figure 11B:
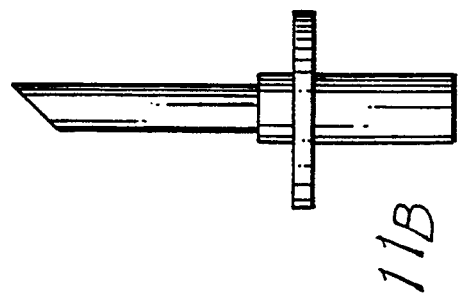
FIG. 11B is a elevation view of a beveled spiking pin.
Figure 10B:
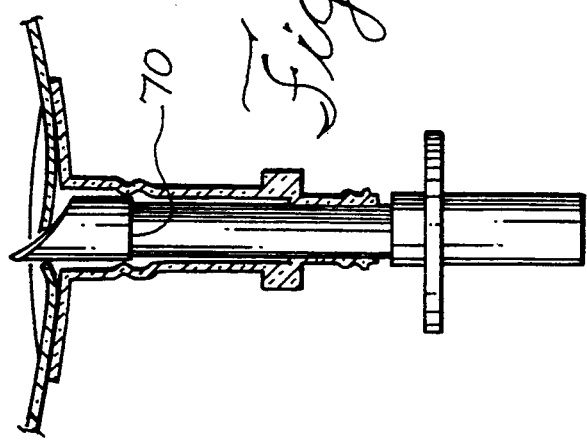
FIG. 10B is a elevation view of a blunt spiking pin.
Figure 11A:
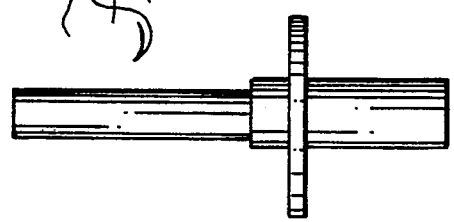
FIG. 11A is a partial cross section of the port assembly according to the present invention when activated by a beveled spiking pin.
Figure 9A:
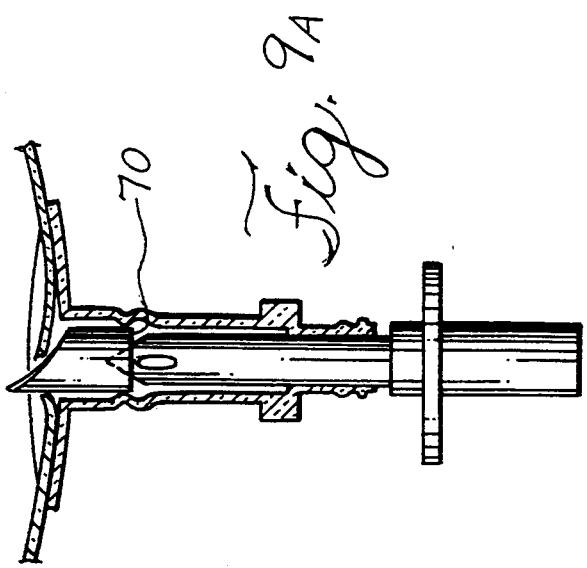
FIG. 9A is a partial cross section of the port assembly according to the present invention when activated by a center point spiking pin.
Figure 9B:
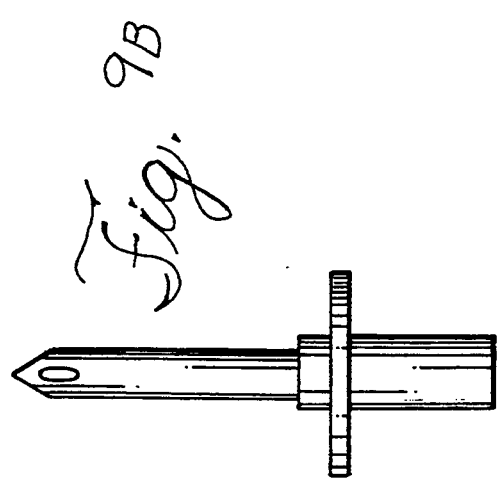
FIG. 9B is a elevation view of a center point spiking pin.

As shown in FIGS. 9, 10, and 11, the second end 70 of the penetrator is able to adapt to any convention piercing pin configuration. Fluid flow through the penetrator is assured by either the primary center throughbore 66 or the secondary longitudinal channel 68 along the outside cylindrical edge.

The fluid sump 30 on the bottom surface of the flexible container and the flow passageways 66 and 68 in the penetrator 60 facilitates less residual solution remaining in the bottom of the flexible solution container. A greater percentage of the solution in the flexible container will be readily available for flow communication through the administration ports. The hollow chamber 64 in the beveled end 62 of the penetrator facilitates that any solution in the sump will be able to flow through either the center bore or the longitudinal channel of the penetrator to the access fitment and the administrator set. Thus the fluid sump of the flexible container and the penetrator of the administration port according to the present invention facilitates more drainage of the medical solution than the currently known and used flexible containers.

A sterile formed, filled and sealed packaging method will now be described with reference to FIG. 12. A continuous, longitudinal strip of multiple layer film 82 is provided in rolls 84. The film is unwound and sterilized according to a predetermined, continuous indexing movement.

The film is continuously indexed and longitudinally moved through the sterile core 22 of the packaging line. With the film in a horizontal orientation a uniformally and outwardly stretched plurality of fluid sumps 30 are formed along the center portion of continuous film strip. One method of forming of the sumps 30 is to apply heat to the film and use the outward movement of a forming mandrel. An alternative method for uniformally and outwardly stretching discrete center portions of the film strip is to apply heat and a vacuum from the outside or bottom edge of the film strip.

Once the film strip has been permanently stretched to form fluid sumps 30 along the saddle line of the film, a rigid tubular port assembly 12 having a circumferential flange 56 at one end is attached to the sump 30, preferably by thermal bonding. The inner face of the flange is congruent with the outwardly stretched configuration of the fluid sumps to provide annular sealing around the orifice of the tubular port member. Preferably the relevant portion of the film at the sump is heated and the flange of the port member is heated and a circumferential seal is created around the flange member by application of a thermal bonding process. Alternatively, other bonding processes such as heat and pressure, ultrasonic welding, or even adhesive bonding could be used.

With the port assembly 12 now firmly bonded to the outer face of the laminated film, the wings of the flat film sheet are formed or plowed into a continuous U-shaped trough so as to define the side walls of the container. The bottom surface 40 includes the sump and circumferentially sealed saddle flange and the two opposed portions of the inner layer of the multiple layer film define the side walls.

A first portion of the opposed inside layers of the film strip are formed together in a first transverse side seal 42 that extends from the bottom surface 40 to the outer edge of the film strip. The transverse side seal is generally perpendicular to the bottom surface. As the continuously indexing advances the film through the packaging line, a second portion of the opposed inside layer of the strip is formed together to form a second parallel transverse side seal 44 extending from the bottom surface 40 to the top edge. The first side seal 42, the bottom surface 40, and the second side seal 44 define an open pouch.

The pouch is advanced along the packaging line and is optionally flushed with a flushing agent, such as $N_2$ to remove all the air from the pouch pocket as needed. A sterile solution is then metered through a filling nozzle into the pouch and displaces the flushing agent or sterile air as provided.

When the pouch is filled with the metered sterile solution, a third portion along the top of the folded film strip is sealed together to form a top seal 46 and thus complete the hermetically sealed flexible container containing the sterile solution. At this point in the process, the continuous strip of filled flexible containers can exit the sterile core. Preferably the film strips are cut coincident with (i.e. in the middle of) the first and second side seals 42 and 44 so as to divide the continuously formed, filled and sealed film strips into individual sealed containers. Although this cutting step may be performed inside the sterile core, it is preferable to perform cutting outside the core since scrap or particulate will not accumulate in the sterile core.

Thus an individually sealed sterile container having a sterile port assembly and containing a sterile fluid is produced. Since all of the individual components, namely the film, the port assembly, and the sterile solution have been separately sterilized and are brought together in the sterile core, there is no need for further sterilization. This allows heat sensitive drugs, for example, to be package in flexible containers without degradation of the solution due to overheating during a traditional terminal sterilization process such as autoclaving.

Since the diaphragm of the port assembly 12 is the laminated flexible film, there is no lower permeability in the attached port system such as encountered in the previously known and described flexible containers. Thus there is no need for an overwrap material for the flexible container and port assembly of the present invention, nor is there a need for a terminal sterilization process. This invention thus allows new and previously sensitive solutions to be package in form, fill and sealed flexible containers.

While several embodiments of the invention have been described, modifications within the scope of the present invention may be readily apparent to one of ordinary skill in the art. All such modifications are intended to be covered by the scope of the accompanying claims.

We claim:

1. A port assembly for use with a flexible solution container, the flexible container having a hermetically sealed inner chamber and an exposed outer surface formed from a multiple-layer, flexible film, the port assembly comprising:
    a tubular member having a first and a second open end;
    means for attaching the first open end of the tubular member to the outer surface of the flexible container;
    means for fluid flow connection at the second open end of the tubular member;
    means in the tubular member for slidably puncturing the flexible film and penetrating the inner chamber; and
    means in the tubular member for fluid passage from the punctured inner chamber to the fluid flow connection means.

2. The port assembly of claim 1 wherein the means for slidably puncturing the inner chamber is a cylindrical penetrator, the cylindrical penetrator having a hollow beveled end at the first open end of the tubular member for slidably puncturing the flexible film and penetrating the inner chamber.

3. The port assembly of claim 2 wherein the fluid passage means includes a center bore from the hollow beveled end of the penetrator through the cylindrical penetrator.

4. The port assembly of claim 3 wherein the fluid passage means further includes a longitudinal passageway substantially along the outer cylindrical surface of the penetrator and radially connected to the hollow beveled end of the penetrator.

5. The port assembly of claim 4 wherein the means for attaching the tubular member to the outer surface of the flexible container is an integral circumferential flange surrounding the first open end of the tubular member and having a flange face circumferentially sealable to the outer surface of the flexible container.

6. The port assembly of claim 5 wherein the fluid flow connection at the second open end of the tubular member is a fluid tight connector.

7. The port assembly of claim 6 further including a removable cover for closing the fluid tight connector at the second open end of the tubular member.

8. The port assembly of claim 1 wherein the tubular member is a rigid tubular member having an integral circumferential saddle flange at the first open end.

9. A port assembly for use with a flexible, multiple-layer film container having a laminated outer surface and a hermetically sealed inner chamber, the port assembly comprising:
    a rigid tubular body having a first and a second open end;
    a integral circumferential flange surrounding the first open end of the tubular body and having a flange face circumferentially sealable to the outer surface of the container;
    a fluid flow fitment at the second open end of the tubular body;
    a removable cover attachable to the fluid flow fitment for closing the second open end of the tubular body; and
    a cylindrical penetrator slidably contained within the tubular body and having a hollow beveled end for slidably protruding beyond the circumferential flange so as to pierce the surface of the flexible container and penetrate the hermetically sealed inner chamber of the flexible container and at least one passageway through the penetrator for fluid communication from the penetrated inner chamber of the flexible container to the fluid flow fitment.

10. The port assembly of claim 9 wherein the at least one passageway includes a center through bore from the hollow beveled end through the cylindrical penetrator.

11. The port assembly of claim 10 wherein the at least one passageway includes a longitudinal channel on the surface of the cylindrical penetrator and a radial connection with the hollow beveled end of the penetrator.

12. A sterile formed, filled and sealed flexible container for a sterile fluid, the container comprising:
   a flexible film sheet having at least an inner film layer and an outer film layer;
   a longitudinally extending saddle line dividing the film sheet into substantially equal first and second portions;
   a fluid sump stretched outwardly from the film sheet and having a longitudinal axis coincident with the saddle line;
   the first portion of the film sheet folded over the saddle line so that the inner layer of the first portion of the film sheet opposes the inner layer of the second portion of the film sheet;
   a continuous peripheral seal between the inner layer of the opposed first and second portions of the film sheet so as to form a hermetically sealed inner chamber between the first and second portions of the film sheet;
   a rigid tubular port having a first and second open end;
   an integral circumferential flange surrounding the first open end of the tubular port, the flange having a contoured face circumferentially sealed to the outer layer of the film sheet along the radiused fluid sump;
   an access fitment at the second open end of the tubular port;
   a removable cover for closing the second open end of the tubular port;
   a penetrator element slidably contained within the tubular port and having a sharp end for slidably protruding beyond the circumferential flange so as to piece the film sheet and penetrate the sealed inner chamber; and
   at least one passageway through the penetrator element from the sharp end for fluid communication from the penetrated inner chamber to the access fitment.

13. The flexible container of claim 12 wherein the at least one passageway includes a center through bore from the sharp end.

14. The flexible container of claim 13 wherein the at least one passageway includes a substantially longitudinally extending channel along the cylindrical surface of the penetrator and connected to the center through bore.

* * * * *